United States Patent [19]
Damien et al.

[11] Patent Number: 5,563,124
[45] Date of Patent: Oct. 8, 1996

[54] OSTEOGENIC PRODUCT AND PROCESS

[75] Inventors: Christopher J. Damien, Denver; James J. Benedict, Golden, both of Colo.; James W. Poser, Lawrenceville, N.J.

[73] Assignee: Intermedics Orthopedics/ Denver, Inc., Wheat Ridge, Colo.

[21] Appl. No.: 152,519

[22] Filed: Nov. 16, 1993

Related U.S. Application Data

[63] Continuation-in-part of Ser. No. 689,459, Apr. 22, 1991, Pat. No. 5,290,763.
[51] Int. Cl.$^6$ .............................. A61F 2/28; A61F 2/32; A61F 2/44; A61K 38/18
[52] U.S. Cl. .............................. 514/21; 623/16; 623/17; 623/22
[58] Field of Search .............................. 424/549; 530/412, 530/414, 355, 350, 397, 398, 399, 840; 514/2, 8, 12, 21; 623/16, 17, 22, 23

[56] References Cited

U.S. PATENT DOCUMENTS

| | | | |
|---|---|---|---|
| 3,318,774 | 5/1967 | Dingwall et al. | 424/549 |
| 3,458,397 | 7/1969 | Meyers et al. | 424/549 |
| 4,294,753 | 10/1981 | Urist | 530/395 |
| 4,356,572 | 11/1982 | Guillemin et al. | 623/16 |
| 4,361,471 | 11/1982 | Kosarek | 204/128 |
| 4,394,370 | 7/1983 | Jefferies | 424/549 |
| 4,434,094 | 2/1984 | Seyedin et al. | 530/416 |
| 4,440,750 | 4/1984 | Glowacki et al. | 424/572 |
| 4,455,256 | 6/1984 | Urist | 530/350 |
| 4,563,350 | 1/1986 | Nathan et al. | 514/21 |
| 4,596,574 | 6/1986 | Urist | 623/16 |
| 4,608,199 | 8/1986 | Caplan et al. | 530/414 |
| 4,619,989 | 10/1986 | Urist | 530/417 |
| 4,620,327 | 11/1986 | Caplan et al. | 623/10 |
| 4,627,853 | 12/1986 | Campbell et al. | 623/16 |
| 4,627,982 | 12/1986 | Seyedin et al. | 424/549 |

(List continued on next page.)

OTHER PUBLICATIONS

Aspenberg, et al., "Dose–Dependent Stimulation of Bone Induction by Basic Fibroblast Growth Factor in Rats", pp. 481–484, 1991, *Acta Orthop Scand*, vol. 62(5).

Block, et al., "Glycol Methacrylate Embedding Technique Emphasizing Cost Containment, Ultrarapid Processing, and Adaptability to a Variety of Staining Techniques", pp. 290–298, 1982 *Lab. Med.*, vol. 13, May.

Cuevas, et al., "Basic Fibroblast Growth Factor (FGF) Promotes Cartilage Repair in Vivo," pp. 611–618, 1988, *Biochem. and Biophys. Research Comm.*, vol. 156(2), Oct.

Frenkel, et al., "Fibroblast Growth Factor: Effects on Osteogenesis and Chondrogenesis in the Chick Embryo," pp. 265–268, 1992, *Acta Anatomica*, vol, 143. No. 3, Nov.

Guillemin, et al., "Comparison of Coral Resorption and Bone Apposition with Two Natural Corals of Different Porosities," pp. 765–779, 1989, *J. Biomed. Mater. Res.*, vol. 23.

Guillemin, et al., "The Use of Coral as a Bone Graft Substitute," pp. 557–567, 1987, *J. Biomed. Mater. Res.*, vol. 21.

(List continued on next page.)

*Primary Examiner*—Jeffrey E. Russel
*Attorney, Agent, or Firm*—Sheridan, Ross & McIntosh

[57] ABSTRACT

Disclosed is a product which includes calcium carbonate and bone growth factor useful for the promotion of bone formation when implanted in the body. The calcium carbonate is preferably in the form of aragonite which can be recovered from naturally occurring coral. A preferred bone growth factor of the present invention is a protein mixture purified from bone. Also disclosed is a process for the induction of bone formation which includes implanting the product in a body. The product and process of the present invention are particularly useful in hip replacement operations, knee replacement operations, spinal fusion operations, repair of periodontal defects, treatment of osteoporosis, repair of bone tumor defects and repair of bone fractures.

18 Claims, 3 Drawing Sheets

U.S. PATENT DOCUMENTS

| | | | |
|---|---|---|---|
| 4,637,931 | 1/1987 | Schmitz | 424/426 |
| 4,681,763 | 7/1987 | Nathanson et al. | 424/426 |
| 4,743,259 | 5/1988 | Bolander et al. | 623/16 |
| 4,761,471 | 8/1988 | Urist | 530/350 |
| 4,774,228 | 9/1988 | Seyedin et al. | 514/21 |
| 4,774,277 | 9/1988 | Piez | 514/21 |
| 4,774,322 | 9/1988 | Seyedin et al. | 530/353 |
| 4,789,663 | 12/1988 | Wallace et al. | 514/21 |
| 4,789,732 | 12/1988 | Urist | 530/350 |
| 4,795,467 | 1/1989 | Piez et al. | 623/16 |
| 4,795,804 | 1/1989 | Urist | 530/350 |
| 4,804,744 | 2/1989 | Sen | 530/350 |
| 4,810,691 | 3/1989 | Seyedin et al. | 514/2 |
| 4,843,063 | 6/1989 | Seyedin et al. | 514/2 |
| 4,863,732 | 9/1989 | Nathan et al. | 424/549 |
| 4,877,864 | 10/1989 | Wang et al. | 530/324 |
| 4,888,366 | 12/1989 | Chu et al. | 523/115 |
| 4,968,590 | 11/1990 | Kuberasampath et al. | 530/326 |
| 4,975,526 | 12/1990 | Kuberasampath et al. | 530/356 |
| 4,975,527 | 12/1990 | Koezuka et al. | 530/356 |
| 4,992,226 | 2/1991 | Piez et al. | 264/109 |
| 5,001,169 | 3/1991 | Nathan et al. | 523/113 |
| 5,106,748 | 4/1992 | Wozney et al. | 435/252.3 |
| 5,158,934 | 10/1992 | Ammann et al. | 514/21 |
| 5,270,300 | 12/1993 | Hunziker | 530/350 |
| 5,290,763 | 3/1994 | Poser et al. | 514/21 |

OTHER PUBLICATIONS

Hott, et al., "Osteoinductive Effet of Coral Implanted into Rat Bone Marrow," pp. 345–352, 1991, *Cer. in Substit. and Recon. Surg.*

Ohgushi, et al., "Bone Formation Process in Porous Calcium Carbonate and Hydroxyapatite," pp. 885–895, 1992, *J. Biomed. Mater. Res.* vol. 26.

Pouliquen, et al., "Coral as a Substitute for Bone Graft in Posterior Spine Fusion in Childhood," pp. 272–280, 1989, *French J. Orthop. Surg.*, vol. 3(3).

Reddi, "Regulation of Bone Differentiation by Local and Systemic Factors," pp. 27–47, 1985, *Bone and Min. Res.*, vol. 3.

Roux, et al., "Madreporic Coral: A New Bone Graft Substitute for Cranial Surgery," pp. 510–513, 1988, *J. Neurosurg.*, vol. 69, Oct.

Sampath, et al., "Isolation of Osteogenin, an Extracellular Matrix–Associated, Bone–Inductive Protein, by Heparin Affinity Chromatography," pp. 7109–7113, 1987, *Proc. Natl. Acad. Sci. USA*, vol. 84, Oct.

Sautier, et al., "In Vitro Bone Formation on Coral Granules," pp. 1079–1085, 1990, *In Vitro Cell. Dev. Biol.*, vol. 26, Nov.

Shabana, et al., "Ultrastructural Study of the Effects of Coral Skeleton on Cultured Human Gingival Fibroblasts in Three–Dimensional Collagen Lattices," pp. 162–167, 1991, *J. Mater. Science: Mater. in Med.*, vol. 2.

Souyris, et al., "Coral, a New Biomedical Material; Experimental and First Clinical Investigations on Madreporaria," pp. 64–69, 1985, *J. Max.–Fac. Surg.*, vol. 13.

Clin. Orthop., vol. 59, issued 1968, Urist et al, "Inductive Substrates for Bone Formation", pp. 59–96.

PNAS, vol. 85, issued Dec. 1988, Wang et al, "Purification and characterization of other . . . ", pp. 9484–9488.

Molec. Endocrin., vol. 5, issued 1991, Hammonds, Jr. et al, "Bone–Inducing Activity of Mature BMP 2b . . .", pp. 149–155.

Positions 1, 2, 3, 4

OSTEOGENIC PRODUCT AND PROCESS

REFERENCE TO RELATED APPLICATION

This application is a continuation-in-part of, U.S. application Ser. No. 07/689,459, filed on Apr. 22, 1991, now issued as U.S. Pat. No. 5,290,763, which is incorporated herein in its entirety by reference.

BACKGROUND

A number of diseases or injuries involving bones are known for which regeneration of bone is a desired treatment. Formation of bone in vivo involves an interaction of various inductive proteins and growth factors which act by causing a differentiation of mesenchymal cells into cartilage and then bone-forming cell lines. This mechanism is not completely understood. However, in efforts to improve orthopedic procedures, purified protein mixtures or recombinantly produced proteins have been developed which stimulate osteoinductive activity.

While such proteins have been shown to have osteoinductive activity, a difficulty in development of useful products is the identification of suitable delivery vehicles for the proteins. Among the first materials tested for delivery of bone growth proteins was hydroxyapatite. Bone growth protein and hydroxyapatite alone did not demonstrate increased bone formation. Addition of collagen to composites of these materials ameliorated the bone forming response, but the hydroxyapatite remained in the site and was not resorbed.

There exists a continuing need for the development of improved products and processes for the delivery of bone growth factors in treatment of orthopedic diseases and injuries.

SUMMARY

The present invention is directed toward an osteogenic product, comprising calcium carbonate and a bone growth factor. The product can also include a material selected from the group consisting of collagen, fibrin, alginate and mixtures thereof. In a preferred embodiment, the calcium carbonate comprises aragonite. In a further embodiment, the bone growth factor is present at about 10 micrograms bone growth factor/g calcium carbonate and about 1000 micrograms bone growth factor/g calcium carbonate.

The bone growth factor can be selected from the group consisting of purified bone growth factors, recombinantly produced bone growth factors and mixtures thereof. In a preferred embodiment, the bone growth factor comprises an amino acid composition of from about 20.7 to about 26.1 mole percent acidic amino acids, about 11.3 to about 15.7 mole percent hydroxy amino acids, about 37.6 to about 42.4 mole percent aliphatic amino acids, about 5.8 to about 7.9 mole percent aromatic amino acids and about 13.3 to about 19.9 mole percent basic amino acids. The bone growth factor can also comprise, upon hydrolysis, an amino acid composition of from about 20.7 to about 26.1 mole percent ASP(+ASN) and GLU(+GLN); from about 11.3 to about 15.7 mole percent SER and THR; from about 37.6 to about 42.4 mole percent ALA, GLY, PRO, MET, VAL, ILE, and LEU; from about 5.8 to about 7.9 mole percent TYR and PHE; and from about 13.3 to about 19.9 mole percent HIS, ARG, and LYS, based on the total moles of said amino acids.

The present invention is also directed to a process for the induction of bone formation, comprising implanting the product of the present invention in a body. In preferred embodiments, the process is selected from the group consisting of hip replacement operation, knee replacement operation, spinal fusion, repair of periodontal defects, treatment of osteoporosis, repair of bone defects and repair of bone fractures.

DETAILED DESCRIPTION

The present invention is directed toward an osteogenic product which includes calcium carbonate and bone growth factor. The osteogenic product is particularly useful in processes of the present invention which include implanting the product in the body for the purpose of inducing formation of bone.

The calcium carbonate component of the present invention is present in a crystalline form. The calcium carbonate has two important functions in products and processes of the present invention. When implanted in a body with bone growth factor and any optional components of the present product, the calcium carbonate functions as an osteoconductive element. Thus, the calcium carbonate acts as a conductive substrate for bone formation. Calcium carbonate, in the form of natural coral, contains a network of macro- and micropores which allow bone formation through the coral. The interconnected pores of the coral allow bone precursor cells and vessels to invade the coral and implant and provide a large surface area for bone apposition. For example, these pores allow macrophages and osteoclasts or osteoclast-like cells to have access to the interior portion of the coral while increasing the volume available for new bone. In preferred embodiments, the calcium carbonate is resorbable. Over time, coral in the form of aragonite is readily resorbed by the body. The product of the present invention, therefore, allows for formation of bone throughout a defect area without significant residual unresorbed substrate. In contrast, conventional ceramic materials like hydroxyapatite which have been used as bone growth substrates have the potential of remaining in the bone matrix and being more brittle than bone.

Moreover, calcium carbonate is believed to have additional unexpected benefits associated with osteoinduction. As discussed below in more detail in the Example section, the presence of calcium carbonate with bone growth factor in an alginate matrix resulted in bone formation. In the absence of calcium carbonate, however, no bone was formed in the alginate matrix with bone growth factor. Thus, it appears that calcium carbonate has a role in bone formation under some circumstances.

The calcium carbonate of the present invention is preferably in the form of aragonite or calcite. The calcium carbonate is more preferably in the form of aragonite because aragonite is highly resorbable. The calcium carbonate is preferably obtained from the skeletons of coral. Such corals can include, but are not limited to, Acropora, Goniopora, Lobophylla, Porites and mixtures thereof.

The calcium carbonate obtained from these corals are in the crystalline form of aragonite, but have different porosities. For example, Acropora is about 20% porous and Porites is about 50% porous. The use of calcium carbonate having porosities from 0% to more than 50% is within the scope of the present invention. Suitable calcium carbonate of the present invention can be produced by recovering naturally occurring coral, cleaning the coral and sterilizing it. The resulting product can then be examined for fractures, such as by X-ray examination. Sterilization can be accomplished by, for example, subjecting the material to gamma radiation. A preferred calcium carbonate material of the present invention is the material sold under the trademark BIOCORAL by Inoteb of St. Gonnery, France.

Calcium carbonate of the present invention can be used in various forms, including as a block and as particulates. In block form, the calcium carbonate, such as coral, is formed as a unitary article from a larger piece of coral. The unitary article is then used, for example, by being placed in a bone defect or as discussed below in more detail, used in a spinal fusion procedure to fuse two vertebrae.

Alternatively, the calcium carbonate can be in particulate form. Particulates can be produced by, for example, grinding coral to a desired size. Such particulates are typically between about 80 microns and about 3 millimeters, more preferably between about 125 microns and about 2 mm, and even more preferably between about 150 microns and about 1 mm. As discussed below in more detail, particulate forms of calcium carbonate are typically used with a binder, such as collagen, to form a composite which is used to fill a bone defect for induction of bone formation.

The pore diameter of calcium carbonate is large enough such that cells, such as osteoblasts and macrophages, can infiltrate the pores and to allow for capillary formation in the pores. Thus, the pore diameter in calcium carbonate is typically between about 100 microns and about 500 microns, and more preferably between about 150 microns and about 350 microns.

The bone growth factor of the present invention is a protein or mixture of proteins which are capable of inducing bone formation when implanted in a body. It should be noted that while most contemplated applications of the present invention are concerned with use in humans, the products and processes of the present invention work in animals as well. Induction of bone formation can be determined by a histological evaluation showing the de novo formation of bone with accompanying osteoblasts, osteoclasts, and osteoid matrix. For example, osteoinductive activity of a bone growth factor can be demonstrated by a test using a substrate onto which material to be tested is deposited. A substrate with deposited material is implanted subcutaneously in a test animal. The implant is subsequently removed and examined microscopically for the presence of bone formation including the presence of osteoblasts, osteoclasts, and osteoid matrix. A suitable procedure is illustrated in Example 5 of U.S. application Ser. No. 07/689,459 issued as U.S. Pat. No. 5,290,763.

No generally accepted scale for evaluating the degree of osteogenic activity exists, however, certain factors are widely recognized as indicating bone formation. Such factors are referenced in the scale of 0–8 which is provided below in Table 3 of Example 1. The 0–4 portion of this scale corresponds to the scoring system described in U.S. Pat. No. 5,290,763, which is limited to scores of 0–4. The remaining portion of the scale described below, 5–8, references additional levels of maturation of bone formation. The scale described below also includes consideration of resorption of collagen, a factor which is not described in U.S. Pat. No. 5,290,763.

Suitable bone growth factor of the present invention can be produced by purification of naturally occurring proteins from bone or by recombinant DNA techniques. As used herein, the term recombinantly produced bone growth factors refers to the production of bone growth factor using recombinant DNA technology. For example, nucleic acids encoding proteins having osteogenic activity can be identified by producing antibodies that bind to the proteins. The antibodies can be used to isolate, by affinity chromatography, purified populations of a particular osteogenic protein. The amino acid sequence can be identified by sequencing the purified protein. It is possible to synthesize DNA oligonucleotides from the known amino acid sequence. The oligonucleotides can be used to screen either a genomic DNA and/or cDNA library made from, for example bovine DNA, to identify nucleic acids encoding the osteogenic protein. The correct oligonucleotide will hybridize to the appropriate cDNA thereby identifying the cDNA encoding the osteogenic protein encoding gene.

The antibodies that bind osteogenic proteins can also be used directly to screen a cDNA expression library. For example, eukaryotic cDNA sequences encoding osteogenic proteins can be ligated into bacterial expression vectors. The expression vectors can be transformed into bacteria, such as E. coli, which express the transformed expression vector and produce the osteogenic protein. The transformed bacteria can be screened for expression of the osteogenic protein by lysing the bacteria and contacting the bacteria with radioactively-labelled antibody.

Recombinant bone growth factor can be produced by transforming genes identified according to the method described above into cells using any process by which nucleic acids are inserted into cells. After transformation, the cell can produce recombinant bone growth factor by expression of the transformed nucleic acids and such bone growth factor can be recovered from the cells.

A number of naturally occurring proteins from bone or recombinant bone growth factors have been described in the literature and are suitable. Recombinantly produced bone growth factors have been produced by several entities. Creative Biomolecules of Hopkinton, Mass., U.S.A. produces a bone growth factor referred to as Osteogenic Protein 1 or OP1. Genetics Institute of Cambridge, Mass., U.S.A. produces a series of bone growth factors referred to as Bone Morphogenic Proteins 1–8 or BMP 1–8 which are described in U.S. Pat. No. 5,106,748. Purified bone growth factors have been developed by several entities. Collagen Corporation of Palo Alto, Calif., U.S.A. developed a purified protein mixture which is believed to have osteogenic activity and which is described in U.S. Pat. Nos. 4,774,228; 4,774,322; 4,810,691; and 4,843,063. Marshall Urist of the University of California developed a purified protein mixture which is believed to be osteogenic and which is described in U.S. Pat. Nos. 4,455,256; 4,619,989; 4,761,471; 4,789,732; and 4,795,804. International Genetic Engineering, Inc. of Santa Monica, Calif., U.S.A. developed a purified protein mixture which is believed to be osteogenic and which is described in U.S. Pat. No. 4,804,744. All of the foregoing patents are incorporated herein by reference.

Figure 1:
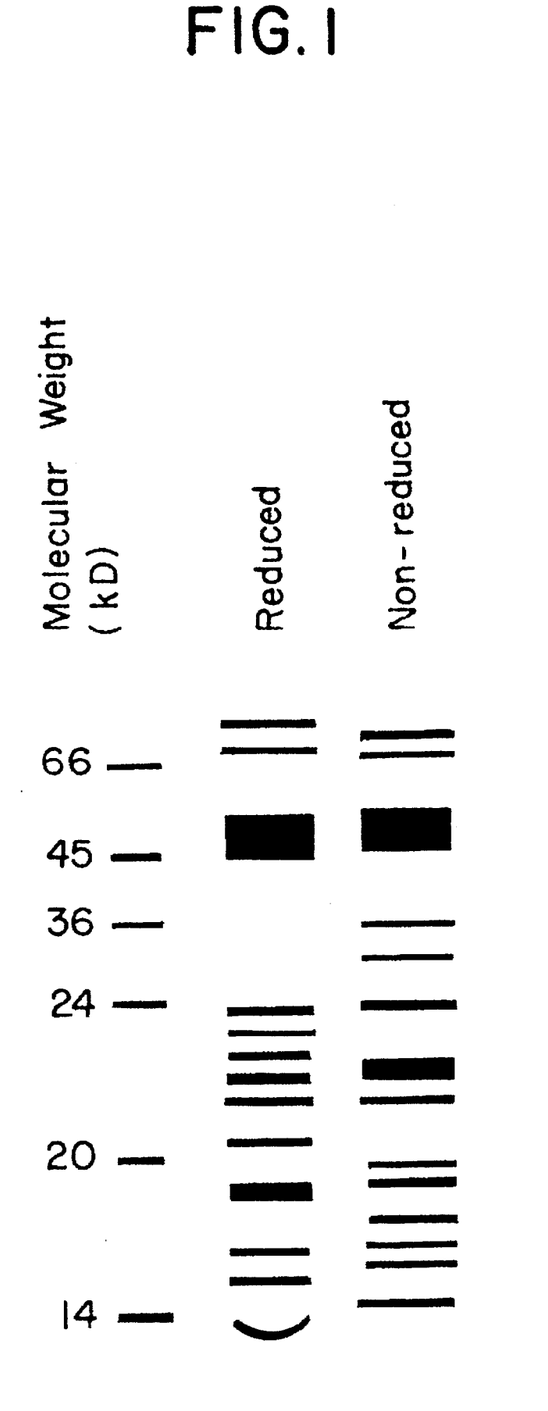
FIG. 1 illustrates an SDS-PAGE of a preferred bone growth factor, both in reduced and nonreduced forms, obtained in accordance with a process of the present invention.

A preferred bone growth factor of the present invention and process for making the same is described in detail in related U.S. Pat. No. 5,290,763. This bone growth factor is particularly preferred because of its high osteogenic activity and because it is a purified bone growth factor. The bone growth factor of U.S. Pat. No. 5,290,763 exhibits osteoinductive activity at about 3 micrograms when deposited onto a suitable carrier and implanted subcutaneously. In one embodiment, the bone growth factor is an osteoinductively active mixture of proteins which exhibit the gel separation profile shown in FIG. 1. This gel separation profile was obtained using SDS-PAGE. The first column is a molecular weight scale which was obtained by performing SDS-PAGE on standards of known molecular weight. The second column illustrates the SDS-PAGE profile for a mixture of proteins in accordance with the present invention which have been reduced with 2-mercaptoethanol. The third column illustrates the SDS-PAGE profile for a non-reduced mixture of proteins in accordance with the present invention. Although the mixture of proteins which provide the SDS-PAGE profile illustrated in FIG. 1 have been found to have high osteoinductive activity, it is anticipated that mixtures of proteins having SDS-PAGE profiles which differ slightly from that illustrated in FIG. 1 will also be effective. For example, effective protein mixtures can include proteins that differ in molecular weight by plus or minus 5 KD from those shown in FIG. 1, and can include fewer or greater numbers of proteins than those shown in FIG. 1. Therefore, mixtures of proteins having profiles which comprise substantially all of the protein bands detected in the reduced or nonreduced SDS-PAGE profiles in FIG. 1 will be considered to be within the scope of the invention.

Yet another embodiment of the preferred bone growth factor of the invention includes an osteoinductively active mixture of proteins having, upon hydrolysis, an amino acid composition of from about 20.7 to about 26.1 mole percent acidic amino acids, about 11.3 to about 15.7 mole percent hydroxy amino acids, about 37.6 to about 42.4 mole percent aliphatic amino acids, about 5.8 to about 7.9 mole percent aromatic amino acids and about 13.3 to about 19.9 mole percent basic amino acids. More particularly, the preferred bone growth factor has an amino acid composition of about 20.7 to about 26.1 (preferably about 23.4) mole percent of ASP (+ASN) and GLU(+GLN); about 11.3 to about 15.7 (preferably about 13.5) mole percent SER and THR; about 37.6 to about 42.4 (preferably about 40.0) mole percent ALA, GLY, PRO, VAL, MET, ILE, and LEU; about 5.8 to about 7.9 (preferably about 6.8) mole percent TYR and PHE; and about 13.3 to about 19.9 (preferably about 16.6) mole percent HIS, ARG, and LYS. A further embodiment of the preferred bone growth factor is a protein mixture having the approximate amino acid composition shown in Table 1.

TABLE 1

| Amino Acid | Mole Percent |
| --- | --- |
| Asp | 11.14 |
| Glu | 12.25 |
| Ser | 9.48 |
| Gly | 8.50 |
| His | 2.28 |
| Arg | 7.19 |
| Thr | 4.03 |
| Ala | 8.05 |
| Pro | 7.16 |
| Tyr | 3.63 |
| Val | 3.79 |
| Met | 1.73 |
| Ile | 2.75 |
| Leu | 8.00 |

TABLE 1-continued

| Amino Acid | Mole Percent |
| --- | --- |
| Phe | 3.21 |
| Lys | 7.11 |

A still further embodiment of the preferred bone growth factor is a protein mixture obtained by any of the purification processes described in U.S. Pat. No. 5,290,763.

A bone growth factor of the present invention is combined with the calcium carbonate in various ways when used in the present invention. For example, when the calcium carbonate is in block form, the bone growth factor is typically put into solution and is then applied to the block. The bone growth factor containing solution then soaks into the porous structure of the block. The solution is then dried, such as by rapid freezing followed by lyophilization, thereby leaving a deposit of the bone growth factor on the block.

Alternatively, when the calcium carbonate is in particulate form, the calcium carbonate particulates can be put into a matrix, such as a collagen, fibrin or alginate dispersion, to form a composite which is then dried. A bone growth factor containing solution is then applied to the dried composite and allowed to soak in. Alternatively, bone growth factor can be mixed into a dispersion which is then mixed with particulate calcium carbonate and dried. Specific examples of particulate form products are described in the Example section.

The amount or dose of bone growth factor used depends on the activity of the bone growth factor and the particular application. In the case of the bone growth factor identified in U.S. Pat. No. 5,290,763, the bone growth factor is used in amounts between about 10 micrograms/gram calcium carbonate and about 10,000 micrograms/g calcium carbonate and more preferably between about 100 micrograms/g calcium carbonate and about 350 micrograms/g calcium carbonate.

Products of the present invention can optionally include components in addition to calcium carbonate and bone growth factor. For example, as noted above, a product can include a matrix forming material, such as collagen, fibrin or alginate. Preferred collagen is Type I bovine tendon atelocollagen. A suitable alginate product is identified in Example 3.

Additional optional components suitable for the present product include other growth factors, such as basic fibroblast growth factor (bFGF) and transforming growth factor beta (TGF-beta) (See Cuevas et al., Basic Fibroblast Growth Factor (FGF) Promotes Cartilage Repair In Vivo, Biochem Biophys Res Commun 156:611–618, 1988). These growth factors have been implicated as cartilage stimulating and angiogenic agents. bFGF, for example, has been shown to increase the rate of osteoblast replication while simultaneously inhibiting their activity (Frenkel S, Singh IJ; The effects of fibroblast growth factor on osteogenesis in the chick embryo. In: Fundamentals of bone growth: Methodology and applications. Ed. AD Dixon, BG Sarnat, D. Hoyte, CRC Press, Boca Raton, Fla., U.S.A., pp. 245–259, 1990). This effect is dose dependent, with higher and lower doses causing decreased activity and middle range doses stimulating activity (Aspenberg P, Thorngren KG, Lohmander LS; Dose-dependent stimulation of bone induction by basic fibroblast growth factor in rats. Acta Orthop Scand 62:481–484, 1991).

The other growth factors described above can be incorporated into products in the same manner as bone growth factors. That is, they can be put into solution and applied to a block of calcium carbonate or a composite of particulate calcium carbonate.

The process of the present invention includes implanting a product which includes calcium carbonate and bone growth factor as broadly described above into a body. As noted above, most uses of the present invention are concerned with human applications. The process, however, is suitable for a wide variety of animals, particularly including other mammals. As used herein, the term implanting refers to placing the product of the present invention in any bone defect or other area in which it is desired to have bone grow. By implanting a product, bone formation is induced by the bone growth factor and the calcium carbonate functions as an osteoconductive agent. Over time, preferred calcium carbonate materials are resorbed allowing for uniform bone formation throughout a defect area.

The present process can be used in a variety of applications whenever there is a need to generate bone. Such applications include induction of bone formation for hip replacement operations, knee replacement operations, spinal fusion procedures, repair of periodontal defects, treatment of osteoporosis, repair of bone tumor defects and repair of bone fractures.

In the case of hip replacement operations, the ball and socket joint of a hip is replaced when a person's hip is not functioning properly. The ball portion of a joint is replaced by surgical removal of the ball portion from the terminus of the femur. The artificial ball portion has a functional ball end with the opposite end being a spike which is inserted into the proximal end of the femur from which the natural ball portion was removed. The spike can have a porous surface so that bone growth around the spike can anchor the spike in the femur. The product of the present invention, in particulate form, is layered or packed between the spike and the cavity in the femur in which spike is to be inserted. The socket portion of a joint is replaced by inserting an artificial socket into the natural socket. The artificial socket is sized to fit with the artificial ball. On the surface of the artificial socket which contacts the natural socket, the artificial socket can have a porous surface. The product of the present invention, in particulate form, is placed in the natural socket cavity so that upon placement of the artificial socket, the product is between the natural and artificial socket. In this manner, as bone is formed, the artificial socket is anchored in the natural socket.

In hip replacement procedures and other procedures which use particulate forms of calcium carbonate, calcium carbonate of varying porosities can be used. Calcium carbonate from the coral Porites is preferred for such applications.

Products of the present invention are also suitable for use in knee replacement operations. Knee prostheses have a femoral and a tibial component which are inserted into the distal end of the femur and the surgically prepared end of the tibia, respectively. The product of the present invention, in particulate form, is layered or packed between the femoral and/or tibial components of the prosthesis and the respective portions of the femur and tibia. In this manner, as bone formation is induced between the prosthesis and the bones, the prosthesis becomes anchored.

Products of the present invention are also suitable for use in spinal fusion operations in which it is desired to substantially immobilize two vertebrae with respect to each other. Typically, the product is in particulate composite form. The composite can be applied, for example, between adjacent spinous and transverse processes so that upon bone formation throughout the composite material, two adjacent vertebrae are joined by fusion between the respective spinous processes and transverse processes. Alternatively, block forms of calcium carbonate can be used. For example, two vertebrae can be fused by positioning one or more blocks of calcium carbonate with bone growth protein between opposing surfaces of the body portion of two adjacent vertebrae in the approximate position of the original disk. The two vertebrae become fused as bone develops between each vertebrae and each side of the block.

When used in spinal fusion procedures and particularly in the latter described procedure in the lower spine, relatively dense calcium carbonate is used. Typically, calcium carbonate which is less than about 35% porous, more preferably less than about 25% porous and even more preferably less than about 10% porous is suitable. For example, calcium carbonate derived from the coral Acropora is preferred for such procedures.

In the case of periodontal defects, the product of the present invention is typically in particulate or composite form and sill conform to the defect shape. As bone growth is induced and the calcium carbonate is resorbed, bone fills in the defect.

In the treatment of osteoporosis, particulate or composite forms of the present product are injected in existing bone to offset the effects of osteoporosis in which bone density is lost. For example, if it is determined that bone density is low in a localized area, such an injection can be made in that area.

EXAMPLES

Example 1

A product comprising natural coral and bone growth factor was tested for the ability of the coral to act as a resorbable osteoconductive carrier matrix for the bone growth factor in subcutaneous sites in rats.

A. Coral Particles

The natural coral implants used comprised the species Porites sp. having an interconnected pore volume of 49±2 percent and a mean pore diameter of 150 µm. Coral particles, measuring 630–710 micrometer (µm) (Inoteb, St. Gonnery, France) were used in this experiment.

B. Bone Growth Factor

Bone growth factor was isolated from the cortical diaphyses of bovine long bones. The marrow and soft tissue was cleaned from the long bones, and the bones were pulverized and demineralized in 1.0 normal (N) hydrochloric acid at a 1:13 weight to volume ratio for 16 hours at 25° C. The bone particles were washed in distilled water and then extracted in a buffered solution comprising of 4N guanidine hydrochloride buffered with 0.1N Tris, pH 7.6 at a concentration of 3 milliliters of buffered solution per gram of original powdered bone. The bone was extracted for 48 h at 15° C. The extracted bone particles were then passed through a series of chromatographic purification steps as described in U.S. Pat. No. 5,290,763 to extract bone growth factor having bone inductive effect at doses less than 35 microgram (µg). The bone growth factor was added to the bovine-derived collagen described above and lyophilized.

C. Carrier Vehicles

Two sets of discs were used for rat subcutaneous implantation assays in rats. One set of discs comprised coral particles combined with a 1 percent dispersion of bovine-derived atelo Type I collagen (American Biomaterials Corp, Plainsboro, N.J.). The second set of discs comprised 350–375 µg of the bone growth factor and collagen mixture described above reconstituted in sterile water added to coral particles. Coral particles combined with collagen with or without bone growth factor were molded into discs, 8 mm in diameter and 3 mm thick, and lyophilized. The formulation was adequate to prepare about 10 discs.

D. Basic Fibroblast Growth Factor

Discs containing purified basic fibroblast growth factor (bFGF) for were also prepared for implantation. bFGF was added to coral particle discs with or without bone growth factor added. 15 nanogram of bFGF (IMEDEX, Chaponost, France) per milligram of coral particle disc was pipetted onto a disc and allowed to soak into the disc.

E. Implantation Procedure

Figure 2:
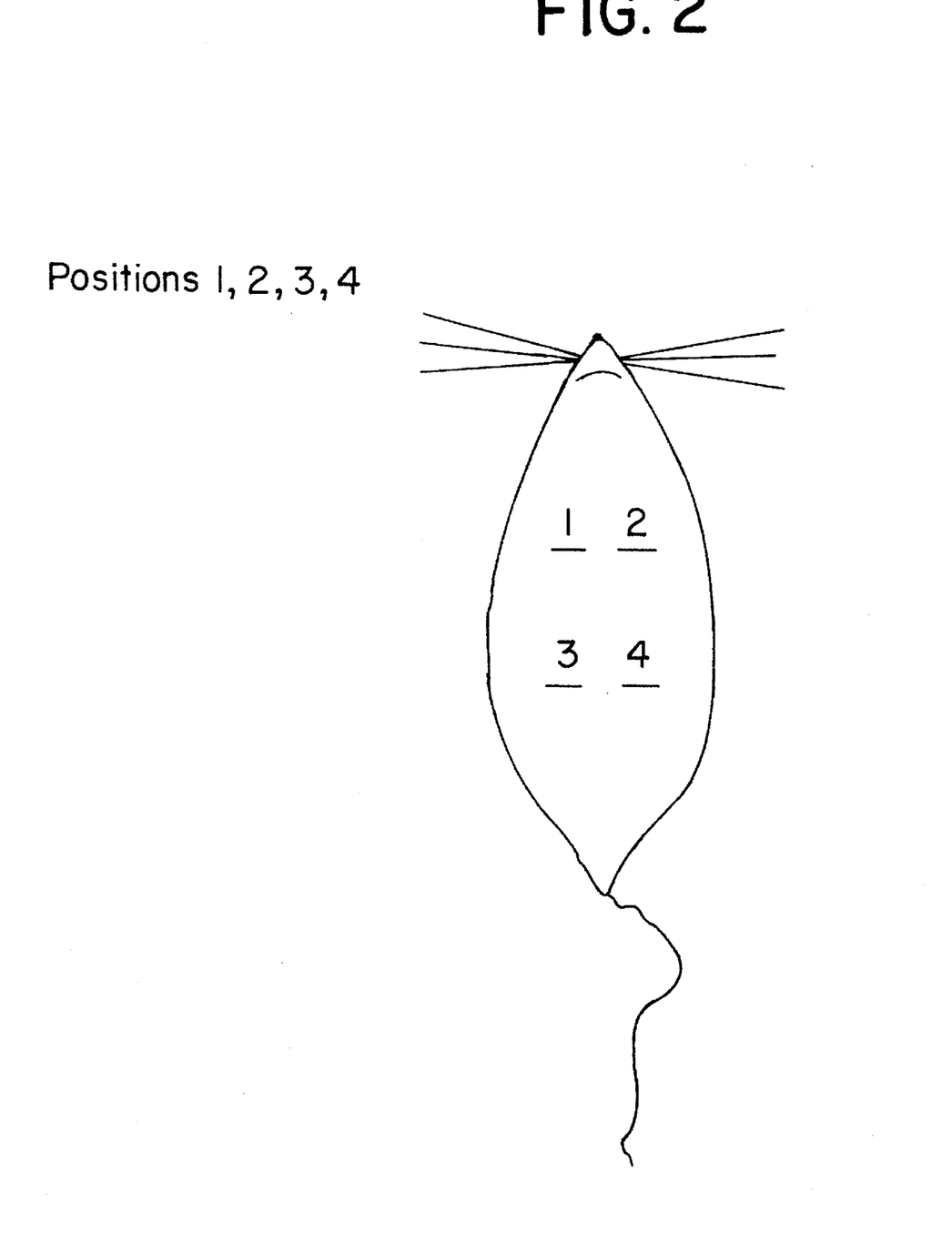
FIG. 2 is a sketch of a rat showing locations of implantations of osteogenic products of the present invention as described in Example 1.

Twenty-one Long-Evans rats were used for this study. The rats were anesthetized using 40 milligram per kilogram of Zoletil 50 (tiletamine hydrochloride and zolazepam hydrochloride; Laboratoires Reading, L'Hay-Les-Roses, France). The rats were shaved and prepared for surgery. Using aseptic techniques, four incisions were made in the ventral region and two on either side of the midline. Subcutaneous pockets were created using blunt dissection and the implants placed into the rats in the locations shown in FIG. 2. Care was taken to avoid cross-reaction of the implants. Incisions were then closed using staples. Table 2 summarizes the distribution of the implants and the time periods studied.

TABLE 2

Distribution of Implants and Sacrifice Times

| IMPLANT MATERIAL | (Number of Implants per Time Period) | | |
|---|---|---|---|
| | 2 WKS | 4 WKS | 8 WKS |
| CC | 7 | 7 | 7 |
| CC:bFGF | 7 | 7 | 7 |
| CC:BGF | 7 | 7 | 7 |
| CC:bFGF:BGF | 7 | 7 | 7 |

CC = Coral:Collagen
BGF = Bone Growth Factor
bFGF = basic Fibroblast Growth Factor F. Histological Analysis of Stained Explants The rats were sacrificed using a lethal intraperitoneal injection of Dolethal. Samples were removed, examined grossly, fixed in 40 percent ethanol, dehydrated in increasing concentrations of ethanol, and infiltrated and embedded in polymethylmethacrylate (PMMA). Samples were cut on a low-speed diamond saw, glued to Plexiglas® slides, ground and polished to 40–60 µm and stained with a combination of Stevenel's blue and Van Gieson picro-fuchsin.

1. Two Week Explants

Twenty-one of twenty-one animals were analyzed. The implants were palpated through the skin and easily visualized at explant. No bone formation was detected using the CC and CC:bFGF implants. Thus, the CC and CC:bFGF implants were used as negative controls. At two weeks, the CC and CC:bFGF samples were infiltrated with fibrous tissue. The remains of the collagen composite were clearly visible at the center of the implant, sometimes undergoing dystrophic mineralization. The coral particulate showed little signs of resorption, especially those particles still surrounded by collagen in the center of the implant. There was no difference in the results of the CC and CC:bFGF implants.

Significant osteoconductive activity was detected in the samples containing bone growth factor removed after two weeks of implantation. Abundant cartilage formation with chondroblasts and extracellular matrix was detected in both the CC:BGF and CC:BGF:bFGF implants. The cartilage formed an inner ring of the ossicle, with more mature mineralizing cartilage and osteoblastic bone formation forming the outer ring. The newly formed bone was immature and woven. The coral particles toward the center of the implant remained virtually unchanged surrounded by unresorbed collagen matrix. Coral particulate toward the outer edge demonstrated some resorption and was either surrounded by cartilage formation or new bone. The samples often exhibited an infarcted character with what appeared to be fluid retention of the collagen "pushing" the coral toward the outer edge.

2. Four Week Explants

No bone formation was detected in explants of the CC and CC:bFGF implants removed at 4 weeks. Some dystrophic mineralization was present in these samples. Increased resorption of coral particles, in particular towards the outer edge of the explant, was detected when the two week CC and CC:bFGF samples were compared with the four week samples. The explants were generally smaller and flatter than the implanted material.

The CC:BGF and CC:BGF:bFGF samples removed at four weeks were mineralized except in one sample where small amounts of cartilage were still evident. Generally, mineralizing cartilage and bone formation via osteoblasts were detected in the samples. Thin layers of osteoblast-derived bone were seen at the outer boundary of the ossicle. Layers of woven bone and mineralized cartilage were detected toward the central areas. Between these two layers there was abundant hematopoietic marrow. Toward the center of the explant, the coral particles remained fairly large and surrounded by fibrous tissue and the remains of the collagen composite. Further out, the coral could be seen surrounded by bone or mineralizing cartilage and appeared to be in the process of resorption indicated by the particles being smaller in size.

3. Eight Week Explants

The CC and CC:bFGF samples implants continued to demonstrate resorption of the coral by macrophages and multinucleated cells when removed after eight weeks of implantation. No bone formation or cartilage, however, was detected.

The CC:BGF and CC:BGF:bFGF samples continued to demonstrate various levels of mature bone formation after eight weeks of implantation. In some CC:BGF samples, the collagen matrix at the center of the ossicle had been completely replaced by trabecular bone and hematopoietic marrow. In addition, very little coral was left in these explants and the coral particles that remained were small and surrounded by new bone. In the remaining CC:BGF samples, two separate layers of bone formation with intervening hematopoietic marrow were present, indicating less mature bone formation. Unresorbed coral particles in the center and resorbing smaller particles toward the outer edge were also detected.

Thus, results from the histological staining indicate implants comprising coral particulate are osteoconductive and resorbable. The results also indicate that bone growth factor, in the presence or absence of bFGF, induces bone formation. bFGF, however, does not contribute to bone formation.

G. Semi-Quantitative Histological Analysis

A semi-quantitative scoring system was used to analyze and compare the amount and maturity of bone formation. Table 3 summarizes histological scores and their identifying characteristics used to analyze the samples. Scores of 1–4 indicate evidence of chondrogenesis. Scores of 5–8 indicate absence of cartilage. A higher score indicates a more mature ossicle.

TABLE 3

Scoring System for Histological Sections

| Score | Characteristic Appearance |
|---|---|
| 0 | No mineralization except dystrophic mineralization<br>Coral size unchanged |
| 1 | Focal areas (<50% of section area) of mineralized tissue of cellular origin<br>Minimal coral resorption |
| 2 | Some mineralization at outer edges<br>Little to no hematopoietic marrow<br>Minimal coral resorption |
| 3 | Mineralized tissue shows circular pattern at outer edges<br>Some hematopoietic marrow<br>Some coral resorption |
| 4 | Clear, but thin, rim of bone at periphery with active osteoblastic surfaces<br>Hematopoietic marrow and coral resorption<br>Some chondrocytes still present |
| 5 | All mineralized tissue osteoblastic, however, randomly oriented and not coherent<br>Large quantity of coral remains |
| 6 | All mineralized tissue osteoblastic; more coherent bone structure at outer edge with gaps<br>Less coral; some still large |
| 7 | All mineralized tissue osteoblastic; continual outer edge of bone<br>Majority of small coral particles |
| 8 | Thick outer bone edge filled with hematopoietic marrow. Bone throughout ossicle<br>Any remaining coral surrounded by bone and in process of resorbing |

Statistical analysis was done using a bilateral paired Student's t-Test and Statview software. Significance was assumed at $p<0.05$.

Figure 3:
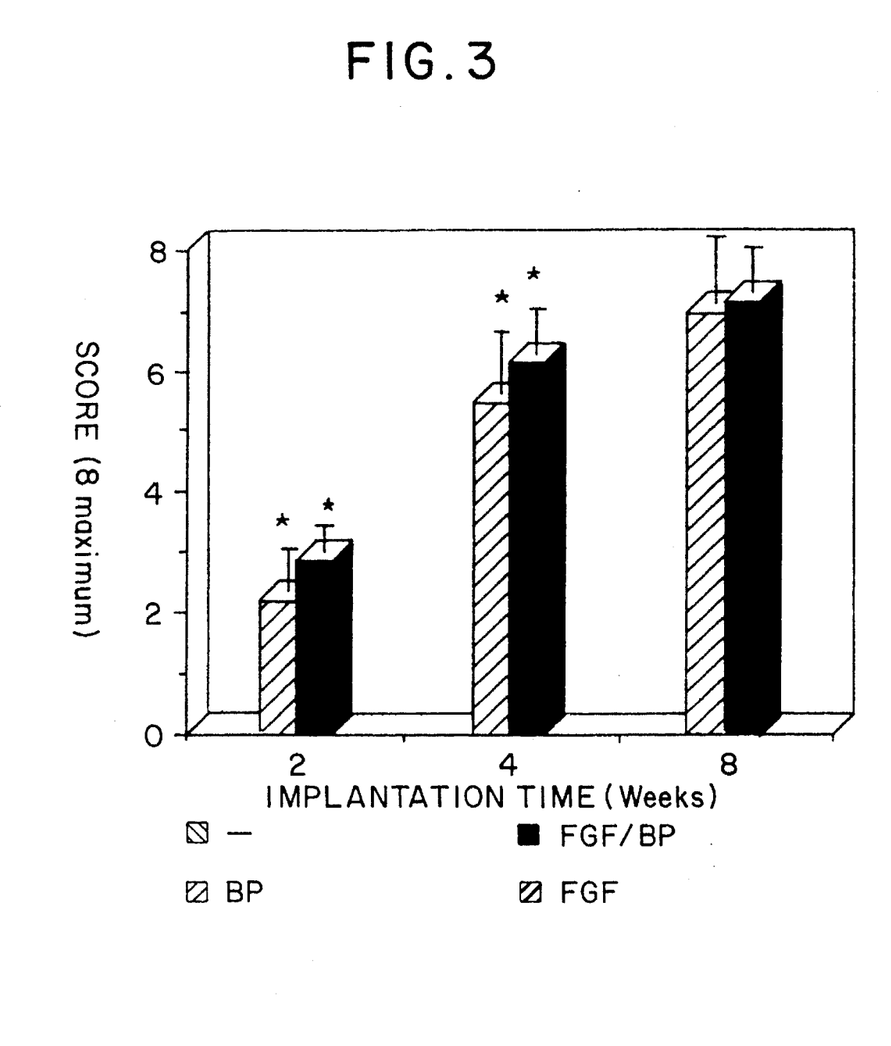
FIG. 3 is a bar graph illustrating the results of histological analysis of product explants comparing osteogenic properties of various products as described in Example 1.

Using the scoring system described in Table 3, histological samples were evaluated as to their cartilage and bone formation capability and the relative maturity of the mineralized tissue. FIG. 3 summarizes the relative maturity over time of the explants depending on the material implanted. The results indicate that implants containing bone growth factor elicited greater chondroinductive and osteoinductive activity than samples without bone growth factor. The maturity of the ossicle of samples containing bone growth factor increased with increasing implantation time. This was also seen qualitatively by an increasing paucity of cartilage and thickening of the outer bony layer. The results also indicate that samples containing both bone growth factor and bFGF showed a higher average statistical increase in maturity than samples with bone growth factor alone ($p<0.05$). The increase, however, was not detected in the four and eight week explants even though the average increase was higher.

Thus, consistent with the histological staining results, the semi-quantitative scoring results indicate that the maturity of ossicles was statistically higher in samples containing bone growth factor compared with samples not containing bone growth factor.

Example 2

This example demonstrates the effectiveness of a calcium carbonate and bone growth factor product to induce bone replacement in defective ulnar bones in rabbits.

The bone formation and coral resorption by CC and CC:BGF composites described in Example 1 were tested in a segmental bony defect model in rabbits. Segments were removed from the ulnar of the forearm of 40 rabbits. Implants having the same shape as the removed segment of ulnar bone, typically about 5 millimeters in diameter and 17 millimeters in length, were fabricated using CC and CC:BGF composites. The implants were surgically placed in the segmental defect in the ulnar as a single piece. Explants were analyzed at 2, 4 and 8 weeks using the histological staining methods described in Example 1.

The results indicate that 2 week explants of ulnar bones bridged using CC:BGF composite showed bridging of the defect. Mineralizing cartilage and bone formation via osteoblasts were detected at the regions where the ulnar bone contacted the CC:BGF composite and thin layers of osteoblast-derived bone were seen at the outer boundary of the CC:BGF boundary. The coral particulate of the CC:BGF composite in the 4 week explants was >90% resorbed and replaced by bone. Virtually all of the coral of the CC:BGF composite was resorbed in the 8 week explants and replaced with trabecular bone and hematopoietic marrow.

The CC explants showed substantially less bone formation and resorption than the CC:BGF explants at all time points.

The results indicate that natural coral provides a moldable bone graft material that can fill non-load bearing bony defects. The CC:BGF composite provides both osteoinductive and osteoconductive properties. In addition, the coral is resorbed at a rate similar to that of new forming bone.

Example 3

This example compares the effectiveness in bone formation of bone growth protein in an alginate matrix with that of bone growth protein and calcium carbonate in an alginate matrix.

Products were prepared by forming discs from either (1) a 4% aqueous dispersion of alginic acid [Sigma A-7128] sodium salt from the kelp *Macrocystis pyrifera* (2% solution) or (2) a 4% aqueous dispersion of alginic acid with coral (particulate Porites 300–450 microns with 50% porosity from Inoteb of St. Gonnery, France) at a 1:1 weight ratio. A dose of 30–35 micrograms of bone growth factor prepared in accordance with Examples 1 and 2 of U.S. Pat. No. 5,290,763 was added to each disc which were then placed in molds and lyophilized. Additionally, control discs were prepared without bone growth factor.

A small (≈6 mm) incision was made in the skin of the ventral thorax region of a female Long-Evans rat, weighing approximately 50 to 100 g. A pocket was prepared beneath the skin by blunt dissection. One of the previously prepared discs containing bone growth factor was inserted in the pocket and the incision was closed with Tevdek II™ (Ethicon) 5-0 sutures. A control disc without bone growth factor was similarly implanted in each animal. The implanted discs were separated from each other by a minimum of 1 cm distance. A group of five rats were prepared with "plus coral" discs and a group of five were prepared with "minus coral" discs. After four weeks, the rats were sacrificed by asphyxiation with carbon dioxide and the test materials were removed.

All control discs and the "minus coral" discs were embedded in poly(glycol methacrylate) and were sectioned into 5 micron sections on a microtome. The "plus coral" discs were embedded in poly(methylmethacrylate), cut on a diamond saw and ground and polished to about 50 microns.

Upon X-ray examination, no bone was evident in the controls or in the "minus coral" discs. X-ray examination was not helpful in determining bone formation in the "plus coral" samples.

Histological analysis of the controls and the "minus coral" samples showed no bone or cartilage formation. Three of the five "plus coral" discs had bone formation as demonstrated by the appearance of cartilage, mineralizing cartilage and bone. The cartilage and bone were located within the alginate network and generally adjacent to coral particles.

The results of this example illustrate that coral has a beneficial effect to enhance formation of bone in a matrix with bone growth factor.

Example 4

This example is directed to rat studies using coral block implants with bone growth factor and no additional carrier.
A. Preparation of Coral Blocks 5×7×2 millimeter rectangular blocks were cut from a larger slab of Porites coral using a diamond saw. The rectangular blocks were cleaned and dried. Five blocks were each uniformly wet with 25 microliters of a 1.43 milligram per milliliter bone growth factor solution in 10 mM HCl. Thus, each block contained a nominal 36 microgram amount of bone growth factor. Five additional blocks were prepared using a 0.14 milligram per milliliter BGF solution. Each block contained a nominal 3.6 micrograms of BGF. All of the blocks were then rapidly frozen on a pre-chilled glass plate at −70° C. and then lyophilized overnight.
B. Skull Implantation 7 millimeter incisions were made in the scalp of anesthetized female Long-Evans rats ranging in weight from 100 to 130 grams. The periosteal membrane was removed by scraping. One BGF containing block was placed on the skull of each of 10 animals. Five animals were implanted with blocks containing 36 micrograms of BGF and 5 animals were implanted with blocks containing 3.6 micrograms of BGF. The incisions were closed with sutures. After 6 weeks, the animals were sacrificed by carbon dioxide asphyxiation. The skulls with the coral blocks attached were removed and fixed in cold methanol. The tissues were dehydrated and embedded in poly(methyl methacrylate). Sections were cut on a low speed diamond saw, ground and polished to about 100 microns.
C. Histological Analysis Histological examination of stained sections demonstrated substantial proliferation of intramembranous bone growing from the calvarial surface up and into the porous spaces of the coral blocks. There was a greater proliferation of new bone at the interface between the skull and the coral block in the 36 microgram dose group then in the 3.6 microgram dose group. In both groups, the bone that formed was mature and lamellar in nature with evidence of bone marrow elements in the intervening spaces. Numerous active osteoblasts and bone forming surfaces were in evidence. The bone that formed in the coral blocks was in intimate contact with the coral surfaces. The coral blocks were rigidly affixed to the rat skulls.

Thus, the results from the histological data indicate that coral, in the presence of BGF and in the absence of additional carrier components such as collagen, induces substantial and efficient bone formation.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following claims.

What is claimed is:

1. An osteogenic product, comprising aragonite and a bone growth factor.

2. An osteogenic product as claimed in claim 1, further comprising a material selected from the group consisting of collagen, fibrin, alginate and mixtures thereof.

3. An osteogenic product as claimed in claim 1, wherein said bone growth factor is selected from the group consisting of purified bone growth factors, recombinantly produced bone growth factors and mixtures thereof.

4. An osteogenic product as claimed in claim 1, wherein said bone growth factor comprises an amino acid composition of from about 20.7 to about 26.1 mole percent acidic amino acids, about 11.3 to about 15.7 mole percent hydroxy amino acids, about 37.6 to about 42.4 mole percent aliphatic amino acids, about 5.8 to about 7.9 mole percent aromatic amino acids and about 13.3 to about 19.9 mole percent basic amino acids.

5. An osteogenic product as claimed in claim 1, wherein said bone growth factor comprises, upon hydrolysis, an amino acid composition of from about 20.7 to about 26.1 mole percent ASP(+ASN) and GLU(+GLN); from about 11.3 to about 15.7 mole percent SER and THR; from about 37.6 to about 42.4 mole percent ALA, GLY, PRO, MET, VAL, ILE, and LEU; from about 5.8 to about 7.9 mole percent TYR and PHE; and from about 13.3 to about 19.9 mole percent HIS, ARG, and LYS, based on the total moles of said amino acids.

6. An osteogenic product as claimed in claim 1, wherein said product comprises between about 10 micrograms bone growth factor/g aragonite and about 1000 micrograms bone growth factor/g aragonite.

7. An osteogenic product as claimed in claim 1, wherein said aragonite is in particulate form.

8. An osteogenic product as claimed in claim 1, wherein said aragonite is in the form of a block.

9. A process for the induction of bone formation, comprising implanting a product, wherein said product comprises aragonite and a bone growth factor.

10. A process as claimed in claim 9 wherein said product further comprises material selected from the group consisting of collagen, fibrin, alginate and mixtures thereof.

11. A process as claimed in claim 9, wherein said bone growth factor is selected from the group consisting of purified bone growth factors, recombinantly produced bone growth factors and mixtures thereof.

12. A process as claimed in claim 9, wherein said bone growth factor comprises an amino acid composition of from about 20.7 to about 26.1 mole percent acidic amino acids, about 11.3 to about 15.7 mole percent hydroxy amino acids, about 37.6 to about 42.4 mole percent aliphatic amino acids, about 5.8 to about 7.9 mole percent aromatic amino acids and about 13.3 to about 19.9 mole percent basic amino acids.

13. A process as claimed in claim 9, wherein said bone growth factor comprises, upon hydrolysis, an amino acid composition of from about 20.7 to about 26.1 mole percent ASP(+ASN) and GLU(+GLN); from about 11.3 to about 15.7 mole percent SER and THR; from about 37.6 to about 42.4 mole percent ALA, GLY, PRO, MET, VAL, ILE, and LEU; from about 5.8 to about 7.9 mole percent TYR and PHE; and from about 13.3 to about 19.9 mole percent HIS, ARG, and LYS, based on the total moles of said amino acids.

14. A process as claimed in claim 9, wherein said product comprises between about 10 micrograms bone growth factor/g aragonite and about 1000 micrograms bone growth factor/g aragonite.

15. A process as claimed in claim 9, wherein said aragonite is in particulate form.

16. A process as claimed in claim 9, wherein said aragonite is in the form of a block.

17. A process as claimed in claim 9, wherein said process is selected from the group consisting of hip replacement operation, knee replacement operation, spinal fusion, repair of periodontal defects, treatment of osteoporosis, repair of bone defects and repair of bone fractures.

18. A process as claimed in claim 9, wherein said process is a hip replacement operation involving the implantation of an artificial hip; said aragonite is in particulate form; and said product is positioned between bone and either the ball or socket portion of the artificial hip.

* * * * *